(12) United States Patent
Furusato et al.

(10) Patent No.: US 8,424,391 B2
(45) Date of Patent: Apr. 23, 2013

(54) ANALYSIS DEVICE PROVIDED WITH FLOW SENSOR, AND FLOW SENSOR ADJUSTMENT METHOD

(75) Inventors: Noriaki Furusato, Kyoto (JP); Yasumasa Honda, Kyoto (JP); Daisuke Takahashi, Kyoto (JP); Minoru Kotaki, Kyoto (JP); Yoshikazu Hirano, Kyoto (JP)

(73) Assignee: Arkray, Inc., Kyoto (JP)

( * ) Notice: Subject to any disclaimer, the term of this patent is extended or adjusted under 35 U.S.C. 154(b) by 147 days.

(21) Appl. No.: 12/737,993

(22) PCT Filed: Sep. 17, 2009

(86) PCT No.: PCT/JP2009/066314
§ 371 (c)(1),
(2), (4) Date: Mar. 8, 2011

(87) PCT Pub. No.: WO2010/032807
PCT Pub. Date: Mar. 25, 2010

(65) Prior Publication Data
US 2011/0174081 A1 Jul. 21, 2011

(30) Foreign Application Priority Data
Sep. 17, 2008 (JP) ................................ 2008-237490

(51) Int. Cl.
*G01F 1/00* (2006.01)
(52) U.S. Cl.
USPC .......................................... 73/861

(58) Field of Classification Search ............... 73/861.04, 73/861
See application file for complete search history.

(56) References Cited

U.S. PATENT DOCUMENTS

| 3,715,709 | A  | * | 2/1973  | Zacharias et al. | ............... | 367/95     |
| 4,655,089 | A  | * | 4/1987  | Kappelt et al.   | ............    | 73/861.356 |
| 6,636,815 | B2 | * | 10/2003 | Keilty et al.    | ..............  | 702/45     |
| 7,360,448 | B2 | * | 4/2008  | Maginnis et al.  | ..........      | 73/861.27  |

FOREIGN PATENT DOCUMENTS

| JP | 56-155815   | A | 12/1981 |
| JP | 62-190469   | A | 8/1987  |
| JP | 63-167222   | U | 10/1988 |
| JP | 02-130471   | A | 5/1990  |
| JP | 11-118819   | A | 4/1999  |
| JP | 2008-134152 | A | 6/2008  |

OTHER PUBLICATIONS

International Search Report mailed on Dec. 22, 2009.

* cited by examiner

*Primary Examiner* — Jewel V Thompson
(74) *Attorney, Agent, or Firm* — Rader, Fishman & Grauer PLLC

(57) ABSTRACT

The present invention relates to a method of adjusting a flow rate sensor 52 for measuring a travel time of a sample passing through a resistive body. The flow rate sensor 52 includes a straight tube 56, and plural photo sensors 52A to 52E for detecting interfaces 82A, 82B between a gas 80 and a liquid 81 traveling in the straight tube 56. Respective positions of the plural photo sensors 52A to 52E are adjusted by detecting the interfaces 82A, 82B by using such photo sensors 52A to 52E.

3 Claims, 29 Drawing Sheets

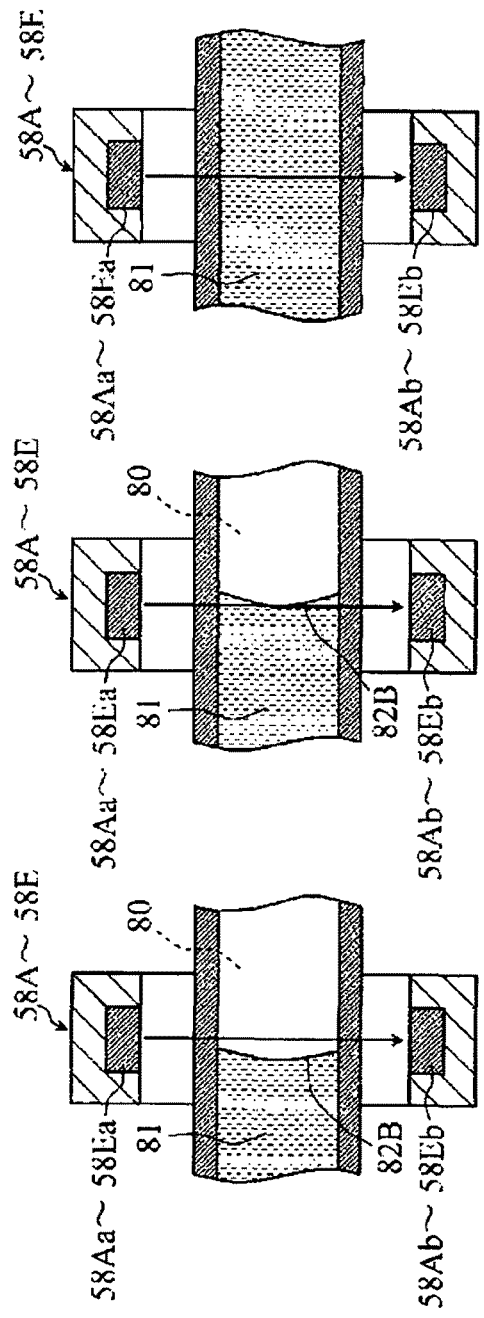

FIG.27A
PRIOR ART
FIG.27B
PRIOR ART
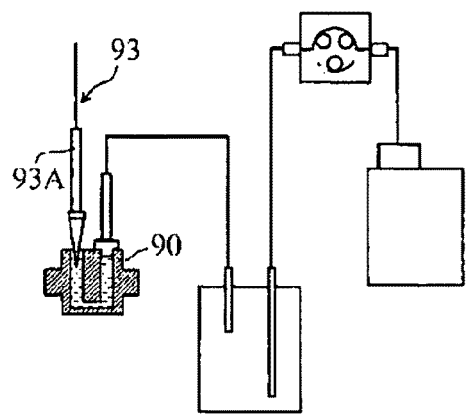
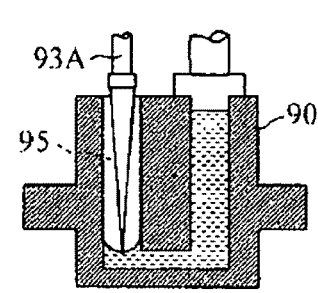

ANALYSIS DEVICE PROVIDED WITH FLOW SENSOR, AND FLOW SENSOR ADJUSTMENT METHOD

TECHNICAL FIELD

The present invention relates to a technology for analyzing a flow property or the like of a sample like a blood sample.

BACKGROUND ART

An example scheme of inspecting a flowability of a blood and a condition of a cell in the blood is a scheme of using a blood filter (see, for example, patent literatures 1 and 2). The blood filter includes a substrate formed with minute grooves and another substrate is joined with that substrate. When such a blood filter is used, a condition of a cell in a blood when the blood passes through the grooves can be observed.

FIG. 25 is a piping diagram showing an illustrative blood inspecting apparatus using the blood filter. A blood inspecting apparatus 9 includes a liquid feeding mechanism 91, a liquid discharging mechanism 92, a blood supply mechanism 93 and a flow speed measuring mechanism 94.

The liquid feeding mechanism 91 is for supplying a predetermined liquid to a blood filter 90, and includes liquid reserving bottles 91A, 91B and a liquid feeding nozzle 91C. The liquid reserving bottle 91A reserves an isotonic sodium chloride solution for measuring a flow speed of a blood. The liquid reserving bottle 91B is for reserving a distilled water used for rinsing pipings. According to this liquid feeding mechanism 91, as a three-way valve 91D is switched accordingly with the liquid feeding nozzle 91C being attached to the liquid filter 90, a state in which the isotonic sodium chloride solution is supplied to the liquid feeding nozzle 91C and a state in which the distilled water is supplied to the liquid feeding nozzle 91C can be selected.

The liquid discharging mechanism 92 is for discharging a liquid in the blood filter 90, and includes a liquid discharging nozzle 92A, a pressure-reduction bottle 92B, a pressure-reduction pump 92C and a liquid discharging bottle 92D. According to this liquid discharging mechanism 92, as the pressure-reduction pump 92C is actuated with the liquid discharging nozzle 92A being attached to the blood filter 90, a liquid in a piping 92E or the like is discharged in the pressure-reduction bottle 92B. The liquid in the pressure-reduction bottle 92B is discharged in the liquid discharging bottle 92D through a piping 92F by the pressure-reduction pump 92B.

The blood supply mechanism 93 suctions a liquid from the blood filter 90 to form a space for retaining a blood, supplies the blood in the space for retaining the blood, and includes a sampling nozzle 93A.

The flow speed measuring mechanism 94 is for obtaining information necessary for measuring a velocity of a blood traveling through the blood filter 90, and includes a U-tube 94A and a measuring nozzle 94B. The U-tube 94A is arranged at a position higher than that of the blood filter 90, and can cause the blood in the blood filter 90 to travel by a water head difference.

According to the blood inspecting apparatus 9, a traveling velocity of a blood is measured as follows.

First, as shown in FIG. 26, the interior of the blood filter 90 is replaced with an isotonic sodium chloride solution. More specifically, the liquid feeding nozzle 91C of the liquid feeding mechanism 91 is attached to the blood filter 90, and the three-way valve 91D is switched so that an isotonic sodium chloride solution in the liquid reserving bottle 91A can be supplied to the liquid feeding nozzle 91C. Meanwhile, the liquid discharging nozzle 92A of the liquid discharging mechanism 92 is attached to the blood filter 90, and the pressure-reduction pump 92C is actuated. Accordingly, the isotonic sodium chloride solution in the liquid reserving bottle 91A is supplied to the blood filter 90 through the liquid feeding nozzle 91C, and the isotonic sodium chloride solution passed through the blood filter 90 is discharged in the liquid discharging bottle 92D through the liquid discharging nozzle 92A.

Next, the liquid feeding nozzle 91C is detached from the blood filter 90, and as shown in FIG. 27A, some of the isotonic sodium chloride solution in the blood filter 90 are suctioned by the sampling nozzle 93A of the blood supply mechanism 93, and as shown in FIG. 27B, a space 95 for retaining a blood is formed.

Furthermore, as shown in FIG. 28A, a blood is collected from a blood collecting tube 96 by the sampling nozzle 93A, and as shown in FIG. 28B, a collected blood 97 is filled in the space 95 of the blood filter 90.

Subsequently, as shown in FIG. 29A, the measuring nozzle 94B of the flow speed measuring mechanism 94 is attached to the blood filter 90. Accordingly, by a water head difference caused between the U-tube 94A and the blood filter 90, the liquid in U-tube 94A travels toward the blood filter 90, and a liquid-level position in the U-tube 94A changes. According to the blood inspecting apparatus 9, as shown in FIG. 29B, a change speed of the liquid-level position in the U-tube 94A is detected by plural photo sensors 98, and based on the detection result, a travel speed of the blood is calculated.

As shown in FIG. 25, the flowability of the blood in the blood filter 90 can be observed on a monitor 99B as an imaging device 99A picks up an image of the blood filter 90.

According to the scheme of utilizing a water head difference between the U-tube 94A and the blood filter 90, however, a liquid-level position in the U-tube 94A changes, so that a measuring pressure (a pressure acting on a blood 97 in the blood filter 90) varies. Moreover, in order to cause the blood 97 to travel in the blood filter 90 by a water head difference, it is necessary that pipings 92E, 94C from the U-tube 94A to the pressure-reduction bottle 92D must be filled with a liquid. Hence, according to the blood inspecting apparatus 9, because a relatively long piping length is requisite, the piping resistance becomes large. Moreover, in addition to the liquid feeding nozzle 91C and the liquid discharging nozzle 92A, the measuring nozzle 94B for supplying a liquid from the U-tube 94A to the blood filter 90 is requisite, the number of nozzles for a measurement is large. Furthermore, because the number of nozzles is large, the pipings become complex, and the number of parts like the number of valves for switching the nozzles 91C, 92A, 93A, and 94B is also large, which interrupts miniaturization of the apparatus. The larger the number of parts becomes, the more a part with a relatively high failure rate like a valve is included, so that a mean-time-between-failure that is an index of representing a failure rate (a performance) of the apparatus becomes short.

In order to overcome such a problem, a straight tube arranged horizontally may be used instead of the U-tube 94A to maintain the water head difference at constant. In this case, however, because an effect to a measured value of a flow speed due to the inconsistency in the internal diameter of the straight tube per product becomes large, it is expected that the flow speed of a blood passing through the blood filter 90 cannot be figured out appropriately. In particular, when the internal diameter of the straight tube is set to be small in order to increase the travel speed of the fluid in the straight tube, the effect to the flow speed due to the inconsistency of the internal diameter becomes further large. Such inconsistency of the flow speed may cause varying in a measurement precision apparatus by apparatus.

Patent Literature 1: Unexamined Japanese Patent Application KOKAI Publication No. H02-130471

Patent Literature 2: Unexamined Japanese Patent Application KOKAI Publication No. H11-118819

DISCLOSURE OF INVENTION

Problem to be Solved by Invention

It is an object of the present invention to reduce the number of parts in an analysis apparatus using a resistive body like a blood filter thereby to accomplish miniaturization of the apparatus, to accomplish cost down and extension of a mean-time-between-failure, and to suppress any varying in a measurement precision apparatus by apparatus.

Means for Solving the Problem

According to a first aspect of the present invention, there is provided an analysis apparatus that includes a flow rate sensor for measuring a travel time of a sample (e.g., a blood) passing through a resistive body. The flow rate sensor includes: a tubular member with a straight part running straightly; and at least one sensor for detecting an interface between a first fluid and a second fluid both traveling in the straight part. The straight part is inclined relative to a horizontal direction. The straight part may be configured to have an inclined angle adjustable relative to the horizontal direction.

It is preferable that at least one sensor should have a position adjustable relative to a direction in which the straight part runs.

The analysis apparatus of the present invention further includes, for example, a piping connected to the downstream side of the tubular member. In this case, it is preferable that the piping should have a larger internal volume than the volume of the second fluid traveling in the tubular member.

According to a second aspect of the present invention, there is provided a flow rate sensor adjustment method in the analysis apparatus of the first aspect of the present invention. According to this adjustment method, a position of the sensor is adjusted by detecting the interface by using the sensor.

According to the flow rate sensor adjustment method of the present invention, it is preferable that the interface should be caused to travel by what corresponds to a predetermined amount of the first fluid and a position of the sensor should be adjusted with respect to the traveled interface.

According to the flow rate sensor adjustment method of the present invention, when at least one sensor includes a plurality of sensors, a sensor located at a most upstream side among the plurality of sensors is aligned with respect to the interface, the interface is repeatedly caused to travel by what corresponds to a predetermined amount of the first fluid, and positions of the sensors other than the sensor located at the most upstream side in the plurality of sensors are adjusted every time the interface is caused to travel.

It is preferable that the inclined angle of the straight tube should be adjusted after a position of the sensor is adjusted. The inclined angle is set in accordance with, for example, a water head difference acting on the straight part.

In the adjustment method of the present invention, typically, the first fluid is a liquid and the second fluid is a gas.

The resistive body is one that gives a travel resistance when, for example, a blood sample travels.

BRIEF DESCRIPTION OF DRAWINGS

FIGS. 12A to 12C are cross-sectional views showing a major part of the flow rate sensor shown in FIG. 10 enlarged in order to explain how it works;

FIG. 27A is a piping diagram for explaining a liquid discharging operation from a blood filter by the blood inspecting apparatus shown in FIG. 25, and FIG. 27B is a cross-sectional view around the blood filter for explaining the liquid discharging operation;

DESCRIPTION FOR REFERENCE NUMERALS

1 Blood inspecting apparatus (analysis apparatus)
2 Blood filter
33 Pressurizing pump
52 Flow rate sensor
53 Pressure-reduction bottle
54 Pressure-reduction pump
58A to 58E Photosensor (of flow rate sensor)
56 Straight tube (of flow rate sensor)
77 Piping
80 Air
81 Blood

BEST MODE FOR CARRYING OUT THE INVENTION

A specific example will be given of a blood inspecting apparatus that is an example of an analysis apparatus of the present invention with reference to the accompanying drawings.

Figure 1:
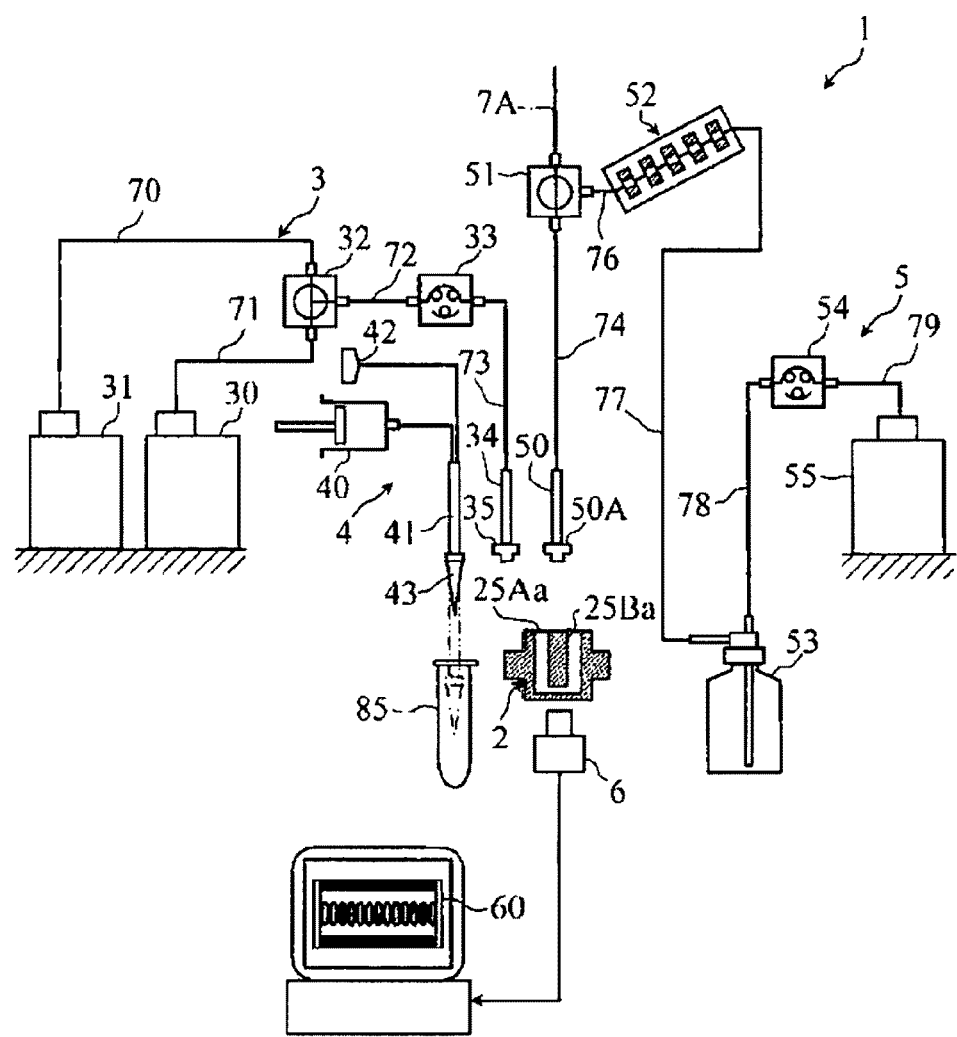
FIG. 1 is a piping diagram showing a blood inspecting apparatus as an illustrative analysis apparatus according to the present invention.

A blood inspecting apparatus 1 shown in FIG. 1 is configured to, using a blood filter 2, measure a flowability of a blood sample like a whole blood, a transformation form of a red blood cell, an activity of a white blood cell, etc. The blood inspecting apparatus 1 includes a liquid supply mechanism 3, a sampling mechanism 4, a liquid discharging mechanism 5 and an imaging device 6.

As shown in FIGS. 2 to 5, the blood filter 2 provides a fluid channel where a blood travels, and includes a holder 20, a fluid-channel substrate 21, a packing 22, a transparent cover 23, and a cap 24.

The holder 20 is for retaining the fluid-channel substrate 21, and enables supply of a liquid to the fluid-channel substrate 21 and discharging of a liquid from the fluid-channel substrate 21. The holder 20 has a pair of small-diameter cylinders 25A, 25B provided in the interiors of a rectangular tube 26 and a large-diameter cylinder 27. The pair of small-diameter cylinders 25A, 25B are formed in a cylindrical shape having respective upper openings 25Aa, 25Ba, and respective lower openings 25Ab, 25Bb, and are integrated together with the rectangular tube 26 and the large-diameter cylinder 27 by fins 25C. The large-diameter cylinder 27 is for fixing the fluid-channel substrate 21, and has a cylindrical recess 27A. The cylindrical recess 27A is a part where the packing 22 is fitted, and a pair of cylindrical convexities 27Aa are formed in the interior of the recess. Provided between the rectangular tube 26 and the large-diameter cylinder 27 is a flange 20A. The flange 20A is used to fix the cap 24 to the holder 20, and is formed in a substantially rectangular shape as viewed from the above. Cylindrical protrusions 20C are provided at respective corners 20B of the flange 20A.

As shown in FIGS. 3, 6, 7A and 7B, the fluid-channel substrate 21 gives a travel resistance when a blood travels, functions as a filter, and is fixed to the large-diameter cylinder 27 (cylindrical recess 27A) of the holder 20 via the packing 22. As shown in FIGS. 6 to 9, the fluid-channel substrate 21 is formed of, for example, a silicon in a rectangular tabular shape as a whole, and has a bank 28 and plural communicating grooves 29 formed by applying a photolithography technique or by performing an etching process on one surface of the tabular silicon.

Figure 6:
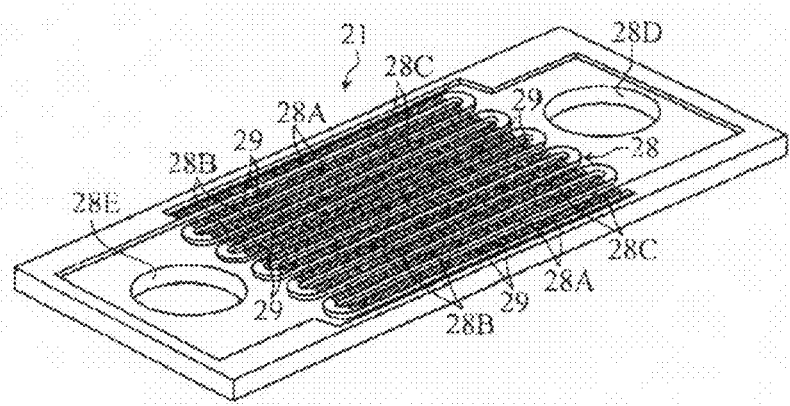
FIG. 6 is an overall perspective view showing a fluid-channel substrate in the blood filter shown in FIG. 2.
Figure 7A:
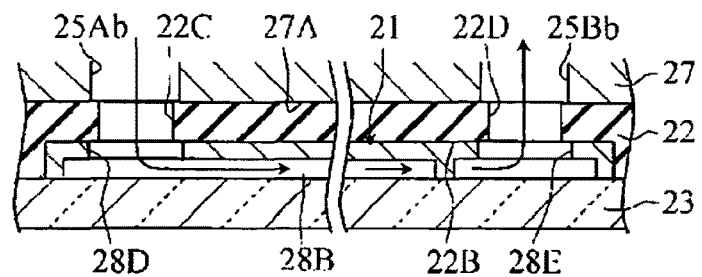
FIGS. 7A to 7C are cross-sectional views showing a major part for explaining the blood filter shown in FIG. 2.
Figure 7B:
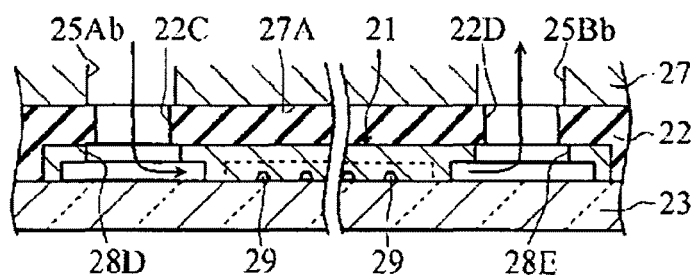
Figure 7C:
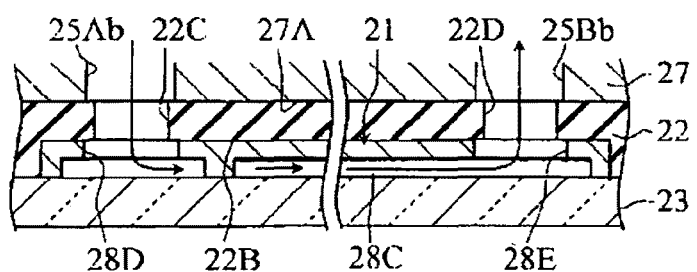
Figure 8A:
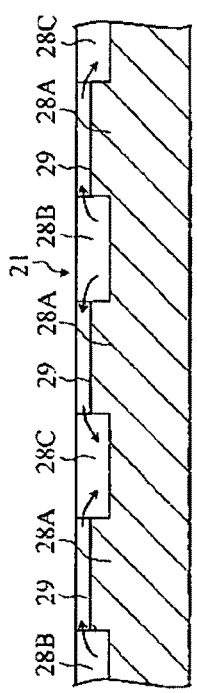
FIG. 8A is a cross-sectional view showing a major part of a cross section along a communicating groove in the fluid-channel substrate shown in FIG. 6.
Figure 8B:
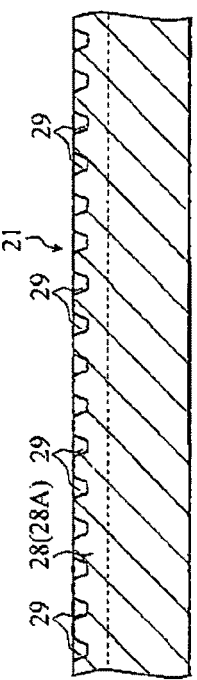
FIG. 8B is a cross-sectional view showing a major part of a cross section along the straight part of a bank in the fluid-channel substrate shown in FIG. 6.
Figure 9:
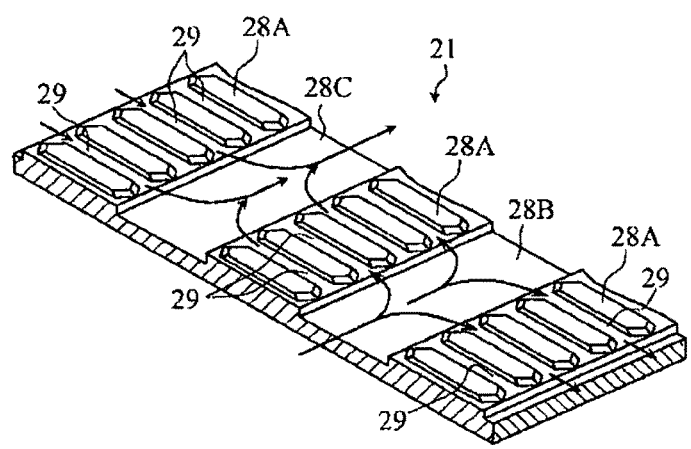
FIG. 9 is a enlarged perspective view showing a major part of the fluid-channel substrate shown in FIG. 6.

The bank 28 is so formed as to serpentine at the center of the fluid-channel substrate 21 in the lengthwise direction. The bank 28 has plural straight portions 28A running in the lengthwise direction of the fluid-channel substrate 21, and an inlet fluid channel 28B and a discharging fluid channel 28C are defined by those straight portions 28A. Through holes 28D, 28E corresponding to respective lower openings 25Ab, 25Bb of the small-diameter cylinders 25A, 25B of the holder 20 are formed at both sides of the bank 28 as shown in FIGS. 6, 7A and 7B. The through hole 28D is for inletting a liquid from the small-diameter cylinder 25A to the fluid-channel substrate 21, and the through hole 28E is for discharging a liquid in the fluid-channel substrate 21 to the small-diameter cylinder 25B.

On the other hand, the plural communicating grooves 29 are so formed as to extend in the widthwise direction of the bank 28 at the straight portions 28A thereof. That is, the communicating grooves 29 cause the inlet fluid channel 28B to be communicated with the discharging fluid channel 28C. Where a transformability of a cell like a blood cell or a blood platelet is observed, each communicating groove 29 is set to have a width dimension smaller than the diameter of a cell, and is set to be, for example, 4 to 6 μm. Moreover, a space between adjoining communicating grooves 29 is set to be, for example, 15 to 20 μm.

According to the fluid-channel substrate 21, a liquid introduced through the through hole 28D successively travels the inlet fluid channel 28B, the communicating grooves 29, and the discharging fluid channel 28C, and is discharged from the fluid-channel substrate 21 through the through hole 28E.

As shown in FIGS. 2 to 5, the packing 22 is for retaining the fluid-channel substrate 21 in the large-diameter cylinder 27 of the holder 20 in a liquid-tight manner. The packing 22 is formed in a discoid shape as a whole, and is fitted into the cylindrical recess 27A of the large-diameter cylinder 27 of the holder 20. The packing 22 is provided with a pair of through holes 22A and a rectangular recess 22B. The pair of through holes 22A are portions where respective cylindrical convexities 27A of the large-diameter cylinder 27 of the holder 20 are fitted. As respective cylindrical convexities 27Aa are fitted in the pair of through holes 22A, the packing 22 is positioned relative to the large-diameter cylinder 27. The rectangular recess 22B is for retaining the fluid-channel substrate 21, and is formed in a shape corresponding to the contour of the fluid-channel substrate 21. However, the depth of the rectangular recess 22B is set to be substantially same as the maximum thickness of the fluid-channel substrate 21 or slightly smaller than that. The rectangular recess 22B is provided with a pair of communicating holes 22C, 22D. Those communicating holes 22C, 22D are for causing respective lower openings 25Ab, 25Bb of the small-diameter cylinders 25A, 25B of the holder 20 to be communicated with the through holes 28D, 28E of the fluid-channel substrate 21.

Figure 3:
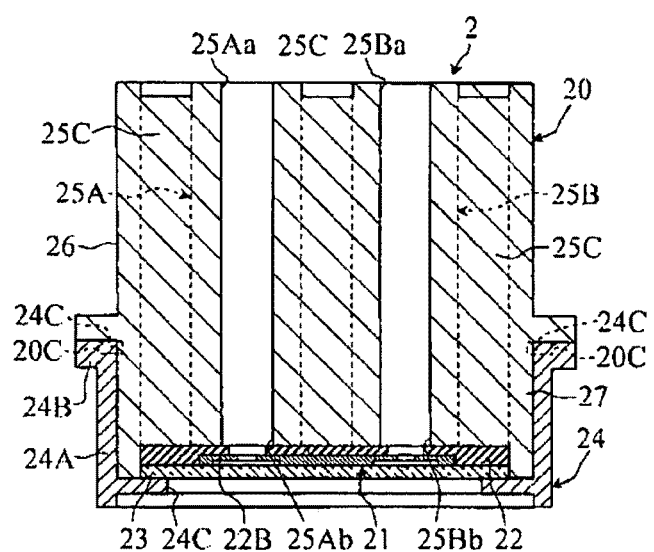
FIG. 3 is a cross-sectional view along a line in FIG. 2.
Figure 4:
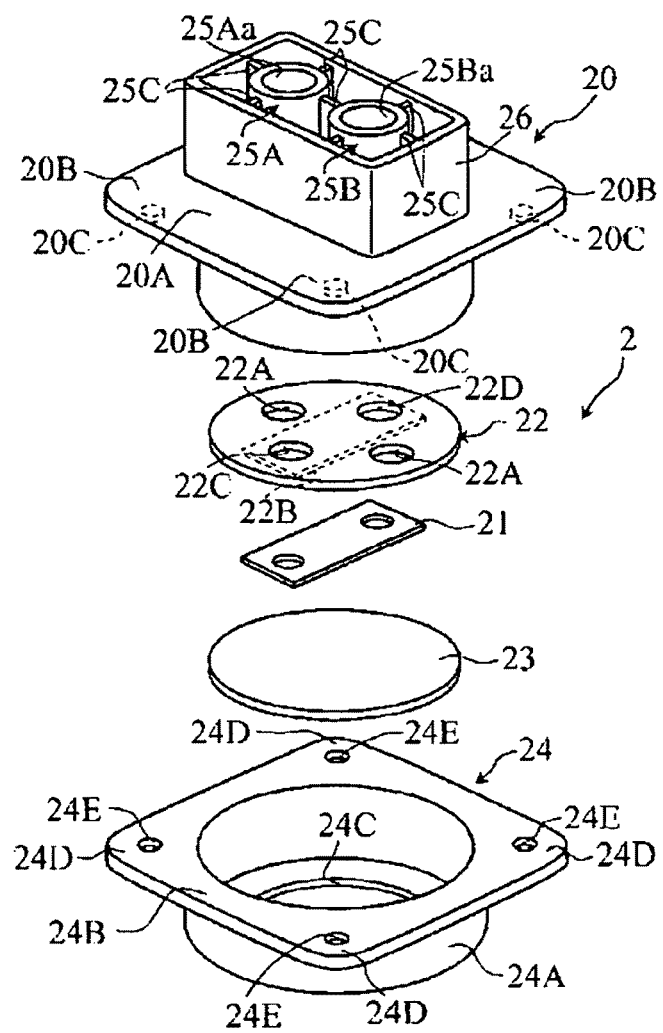
FIG. 4 is an exploded perspective view of the blood filter shown in FIG. 2.
Figure 5:
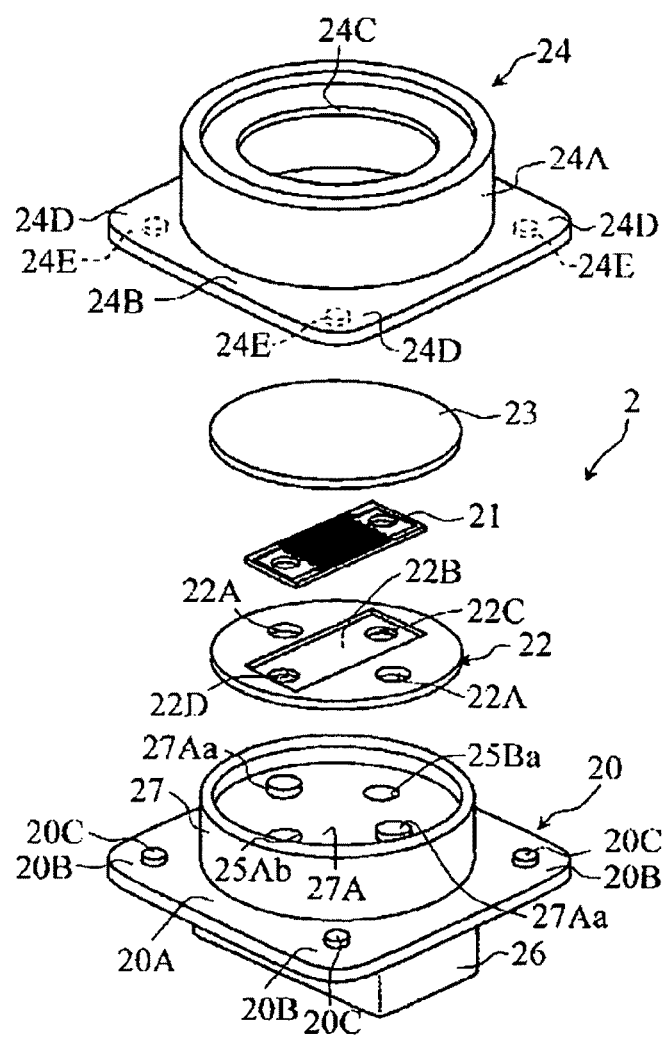
FIG. 5 is an exploded perspective view showing the blood filter shown in FIG. 2 as viewed from a bottom.

As shown in FIGS. 3 to 5, the transparent cover 23 abuts the fluid-channel substrate 21 to cause the inlet fluid channel 28B, the communicating grooves 29, and the discharging fluid channel 28C of the fluid-channel substrate 21 to have a closed cross-sectional structure. The transparent cover 23 is formed of, a glass in a discoid shape. The transparent cover 23 has a thickness set to be smaller than the depth of the cylindrical recess 27A of the large-diameter cylinder 27 of the holder 20, and the total of the maximum thicknesses of the transparent cover 23 and the packing 22 is set to be larger than the depth of the cylindrical recess 27A.

As shown in FIGS. 2 to 5, the cap 24 is for fixing the fluid-channel substrate 21 together with the packing 22 and the transparent cover 23, and has a cylinder 24A and a flange 24B. The cylinder 24A overcoats the large-diameter cylinder 27 of the holder 20, and has a through hole 24C. The through hole 24C is for ensuring the visibility when a travel condition of a blood in the fluid-channel substrate 21 is checked. The flange 24B has a form corresponding to the flange 20A of the holder 20, and has recesses 24E at respective corners 24D. The recess 24E is a part where the cylindrical protrusion 20C of the flange 20A of the holder 20 is fitted.

As explained above, the transparent cover 23 has a thickness which is set to be smaller than the depth of the cylindrical recess 27A in the large-diameter cylinder 27 of the holder 20, and the total of the maximum thicknesses of the transparent cover 23 and the packing 22 is set to be larger than the depth of the cylindrical recess 27A. Conversely, the rectangular recess 22B has a depth set to be substantially same or slightly larger than the maximum thickness of the fluid-channel substrate 21. Accordingly, when the fluid-channel substrate 21 is fixed together with the packing 22 and the transparent cover 23 by the cap 24, the packing 22 is compressed and the transparent cover 23 liquid-tightly contacts the fluid-channel substrate 21 appropriately, so that it is possible to suppress any leakage of a liquid between the fluid-channel substrate 21 and the transparent cover 23.

The liquid supply mechanism 3 shown in FIG. 1 is for supplying a liquid to the blood filter 2, and includes bottles 30, 31, a three-way valve 32, a pressurizing pump 33, and a liquid supply nozzle 34.

The bottles 30, 31 are for reserving respective liquids to be supplied to the blood filter 2. The bottle 30 reserves an isotonic sodium chloride solution used for inspection of a blood, and is connected to the three-way valve 32 by a piping 70. On the other hand, the bottle 31 is for retaining a distilled water for rinsing of the piping, and is connected to the three-way valve 32 by a piping 71.

The three-way valve 32 is for selecting a kind of a liquid to be supplied to the liquid supply nozzle 34, and is connected to the pressurizing pump 33 by a piping 72. That is, by switching the three-way valve 32 as needed, either one of the states: a state in which the isotonic sodium chloride solution is supplied to the liquid supply nozzle 34 from the bottle 30; and a state in which the distilled water is supplied to the liquid supply nozzle 34 from the bottle 31 can be selected.

The pressurizing pump 33 provides power for moving a liquid from the bottles 30, 31 to the liquid supply nozzle 34, and is connected to the liquid supply nozzle 34 by a piping 73. Various kinds of conventionally known pumps can be used as the pressurizing pump 33, but from the standpoint of miniaturization of the apparatus, it is preferable to use a tube pump.

The liquid supply nozzle 34 is for supplying a liquid from each bottle 30, 31 to the blood filter 2, and is attached to the upper opening 25Aa of the blood filter 2. The liquid supply nozzle 34 has a joint 35 which is attached to the upper opening 25Aa (see FIGS. 2 and 3) of the small-diameter cylinder 25A in the blood filter 2, and has another end connected to the pressurizing pump 33 by a piping 73.

The sampling mechanism 4 is for supplying a blood to the blood filter 2, and includes a sampling pump 40, a blood supply nozzle 41, and a liquid-level detecting sensor 42.

The sampling pump 40 is for providing power for suctioning/delivering a blood, and comprises, for example, a syringe pump.

The blood supply nozzle 41 is used with a chip 43 being attached to a leading end thereof, and suctions a blood in the interior of the chip 43 from a blood collecting tube 81 as the sampling pump 40 applies a negative pressure to the interior of the chip 43, and delivers the blood as the sampling pump 40 pressurizes the blood in the chip.

The liquid-level sensor 42 is for detecting the liquid level of the blood suctioned into the interior of the chip 43. When the pressure inside the chip 43 becomes a predetermined value, the liquid-level sensor 42 outputs a signal to that effect, and detects that a target amount of blood is suctioned.

The liquid discharging mechanism 5 is for discharging a liquid inside each piping and the blood filter 2, and includes a liquid discharging nozzle 50, a three-way valve 51, a flow rate sensor 52, a pressure-reduction bottle 53, a pressure-reduction pump 54, and a liquid discharging bottle 55.

The liquid discharging nozzle 50 is for suctioning a liquid inside the blood filter 2, and is attached to the upper opening 25Ba (see FIGS. 2 and 3) of the small-diameter cylinder 25B in the blood filter 2. The liquid discharging nozzle 50 has a joint 50A which is provided at a leading end thereof and attached to the upper opening 25Ba of the blood filter 2, and has another end connected to the three-way valve 51 by a piping 74.

The three-way valve 51 is connected to the flow rate sensor 52 by a piping 76, and a piping 7A to be opened to the atmosphere is connected thereto. The three-way valve 51 can select a state in which a liquid is discharged to the pressure-reduction bottle 53 and a state in which air is inlet into a piping 76 through the piping 7A. The three-way valve 51 is provided at the upstream side of the flow rate sensor 52, and air is inlet into a straight tube 56 of the flow rate sensor 52 to be discussed later from the upstream side.

Figure 10:
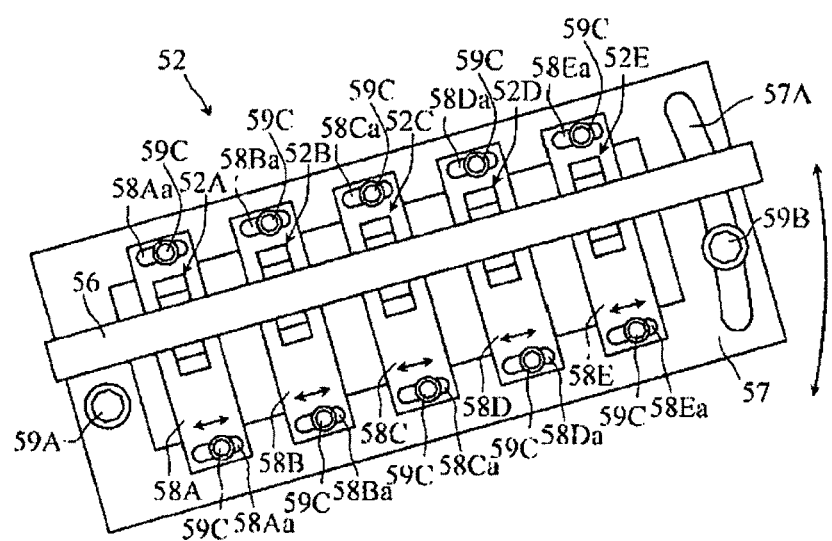
FIG. 10 is a front view showing a flow rate sensor in the blood inspecting apparatus shown in FIG. 1.
Figure 11:
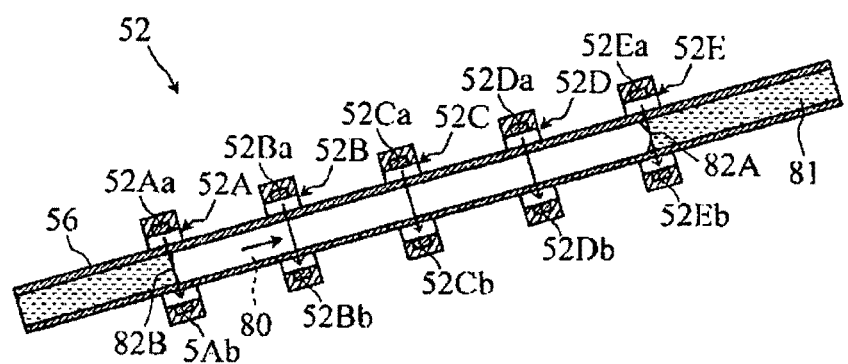
FIG. 11 is a cross-sectional view showing a major part of the flow rate sensor shown in FIG. 10.

As shown in FIGS. 10 to 12, the flow rate sensor 52 is used in order to capture interfaces 82A, 82B between an air 80 and a blood 81 to regulate the inlet amount of air 80, or to measure a travel speed of the blood in the blood filter 2. The flow rate sensor 52 includes plural (in the figures, five) photo sensors 52A, 52B, 52C, 52D, and 52E, the straight tube 56, and a plate 57.

The plural photo sensors 52A to 52E are for detecting whether or not the interfaces 82A, 82B pass through respective areas in the straight tube 56, and are arranged side by side in a horizontal direction with an equal clearance in an inclined condition toward the horizontal direction.

Each photo sensor 52A to 52E comprises a light emitting device 52Aa, 52Ba, 52Ca, 52Da, 52Ea and a photo sensitive device 52Ab, 52Bb, 52Cb, 52Db, and 52Eb, and the flow rate sensor is configured as a transmissive sensor having those devices 52Aa to 52Ea, 52Ab to 52Eb arranged so as to face with each other.

Needless to say, the photo sensors 52A to 52E are not limited to a transmissive type, but a reflective type can be used.

Figure 13A:
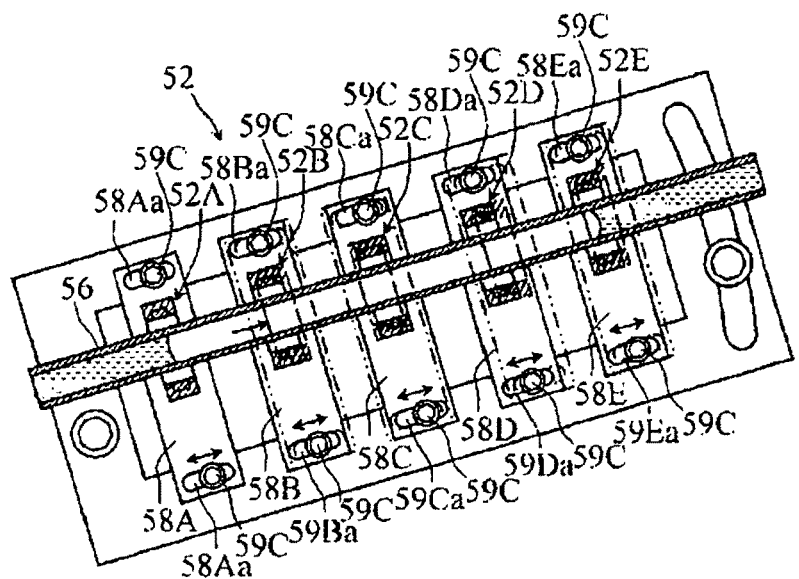
FIGS. 13A and 13B are front views for explaining how the flow rate sensor shown in FIG. 10 works.

As shown in FIG. 13A, each photo sensor 52A to 52E is fixed to each substrate 58A, 58B, 58C, 58D, and 58E, and is movable along the straight tube 56 together with each substrate 58A to 58E. The substrates 58A to 58E are fixed to the plate 57 by bolts 59C through respective slots 58Aa, 58Ba, 58Ca, 58Da, and 58Ea, and can move along respective slots 58Aa to 58Ea by loosening respective bolts 58Aa to 58Ea.

Accordingly, each photo sensor 52A to 52E can move along the straight tube 56 (each slot 58Aa to 58Ea) by moving each substrate 58A to 58E with each bolt 58Aa to 58Ea being loosen, and can be positioned by tightening each bolt 58Aa to 58Ea.

The position of each photo sensor 52A to 52E is adjusted by aligning each of the plural photo sensors 52A to 52E relative to the interface 82B after the upstream-side interface 82B between the air 80 and the liquid 81 is moved by what corresponds to a predetermined amount of the liquid 81.

More specifically, first, with the air 80 being present in the straight tube 56, the photo sensor 52A is aligned with respect to the interface 82A between the air 80 and the liquid 81. This alignment is carried out by moving the substrate 58A along the straight tube 56 while a change in an amount of received light by the photo sensitive device 52Ab of the photo sensor 52A is being checked.

Next, the interface 82A is moved by what corresponds to the predetermined amount of liquid 81. For example, when the flow rate sensor 52 is to detect by a total of 100 μL of the travelling of the amount of the liquid 81 which corresponds to 25 μL, after the photo sensor 52A is aligned, the interface 82A is repeatedly moved by an amount corresponding to 25 μL of the liquid 81, and each photo sensor 52B to 52E is aligned with respect to the interface 82A after movement. Respective photo sensors 52B to 52E are aligned by moving respective substrates 58B to 58E along the straight tube 56 while a change in the amount of received light by respective photo sensitive devices 52Bb to 52Eb is being checked like the case of the photo sensor 52A.

The movement of the interface 82A in the straight tube 56 (supplying of a tiny amount (e.g., 25 μL) of the liquid 81) can be appropriately accomplished by using a highly precise pump with the highly precise pump being connected to the straight tube 56 by a piping. The highly precise pump is typically not built in the blood inspecting apparatus 1, but is prepared separately for alignment of the photo sensors 52B to 52E.

Needless to say, adjustment of the position of each photo sensor 52A to 52E can be carried out by detecting the interface 82A at the downstream side, and can be carried out through other schemes. For example, adjustment can be made based on a first travel time that is measured by detecting the interface 82A between the air 80 and the liquid 81 by using the plural photo sensors 52A to 52E when a straight tube (reference tube) different from the actually installed straight tube is arranged. More specifically, first, a time and a velocity that air (interface) travels between adjoining photo sensors 52A to 52E when the reference tube is installed are measured beforehand. Next, a time and a velocity that the air 80 (interface 82A) travels between adjoining photo sensors 52A to 52E when the straight tube 56 actually built in the apparatus is installed are measured beforehand. Subsequently, when there is inconsistency (e.g., a difference) in the travel time and the velocity between the air when the reference tube is installed and the air 80 (interface 82A) when the straight tube actually used is installed, the photo sensors 52B to 52E with such inconsistency are moved together with respective substrates 58A to 58E, and the distance to the photo sensor 52A is made appropriate. Finally, by tightening all bolts 58Aa to 58Ea, respective positions of the photo sensors 52B to 52E are settled.

As respective positions of the photo sensors 52B to 52E are adjusted in this fashion, the plural photo sensors 52B to 52E can be arranged with a clearance corresponding to the predetermined amount of liquid 81. Therefore, even if there is a difference in the internal diameter of the straight tube 56 actually installed in the apparatus (inconsistency of the internal diameter with that of the reference tube), it is possible to suppress occurrence of a measurement error inherent to such difference. In particular, when the internal diameter of the straight tube 56 is set to be small, it is possible to appropriately suppress occurrence of a measurement error inherent to the difference in the internal diameter.

As shown in FIGS. 10 and 11, the straight tube 56 is a part where the air 80 travels at the time of a measurement, is connected to the three-way valve 51 by a piping 76, and is communicated with the interior of the pressure-reduction bottle 53 through a piping 77 (see FIG. 1). It is preferable that respective internal diameters of the pipings 76, 77 in the vicinity of the straight tube 56 should be same or substantially same (e.g., an internal diameter corresponding to −3% to +3% of an internal area of the straight tube 56) as that of the straight tube 56. The straight tube 56 is fixed to the plate 57 so as to be positioned between each light emitting device 52Aa to 52Ea and each photo sensitive device 52Ab to 52Eb in each photo sensor 52A to 52E and to be inclined with respect to the horizontal direction. The straight tube 56 is formed of a material with a transparency, e.g., a transparent glass or a transparent resin in a cylindrical shape with a uniform cross section. A cylinder with a uniform cross section means a circular cross section with a constant or substantially constant internal diameter (e.g., an internal diameter corresponding to the internal area within a range from −3% to +3% which is a target internal area). The internal diameter of the straight tube 56 can be set to be within a range which enables measurement of a travel speed of the air 80 appropriately, and for example, is set to be 0.9 mm to 1.35 mm which is a smaller internal diameter than those of other pipings. Moreover, in consideration of a dimensional error in the internal diameter, it is desirable that the straight tube 56 should be formed of a transparent glass. This enables more precise measurement of a travel speed of the air 80.

Figure 13B:
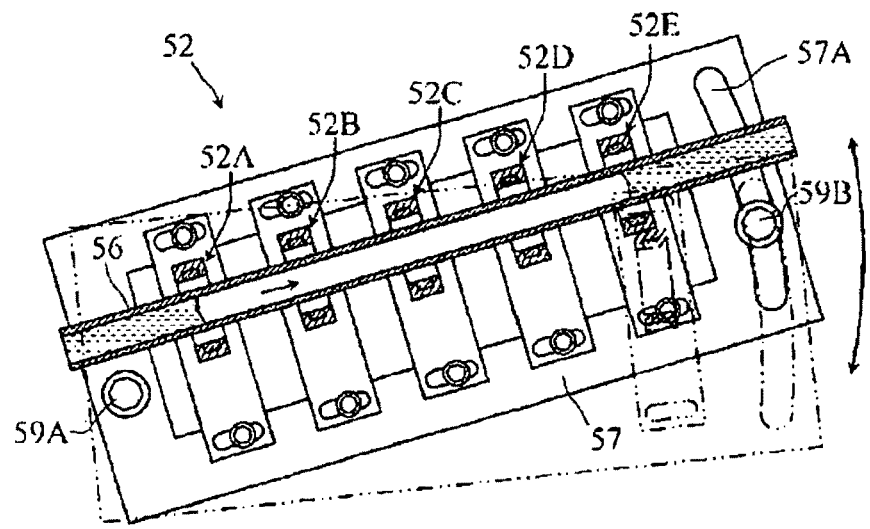

As shown in FIG. 13B, the plate 57 enables adjustment of the inclined angle of the straight tube 56, and is fixed by bolts 59B, 59C. With the bolts 59B, 59C being loosened, the plate 57 is rotatable around the bolt 59B by relatively moving the bolt 59C along the arcuate slot 57A. Accordingly, the straight tube 56 can adjust the inclined angle to the horizontal direction by rotating the plate 57 with the bolts 58Aa to 58Ea being loosened.

The inclined angle of the plate 57 (straight tube 56) is set in accordance with a water head difference acting on the straight tube 56. That is, the water head difference acting on the straight tube 56 includes an error caused among devices due to a difference in the internal diameters of various pipings including the straight tube 56 used in the apparatus, so that if the inclined angle of the straight tube 56 is adjusted, it is possible to suppress occurrence of a measurement error inherent to a difference in water head differences. Note that the inclined angle of the straight tube 56 can be set by utilizing a travel speed and a travel time when the interfaces 82A, 82B are moved in the straight tube 56. In this case, As shown in FIGS. 12A and 12B, when the air 80 (interfaces 80A, 80B) travels in the straight tube 56, a ratio between the isotonic sodium chloride solution and the air 80 at an area corresponding to each photo sensor 52A to 52E gradually changes, so that the amount of received light (transmittance) obtained by the photo sensitive device 52Ab to 52Eb in the photo sensor 52A to 52E changes. Accordingly, the interfaces 80A, 80B can be detected based on a time when the amount of received light (transmittance) obtained by the photo sensor 52A to 52E starts changing or on a time when the amount of received light (transmittance) becomes a constant value after the amount of received light (transmittance) starts changing. When passing of the interfaces 80A, 80B through plural photo sensors 52A to 52E is individually detected, a time when the interfaces 80A, 80B pass through adjoining photo sensors 52A to 52E, i.e., a travel time of the air 80 (interfaces 80A, 80B) can be detected. Moreover, by providing equal to or larger than three photo sensors 52A to 52E, it is possible to measure not only a travel speed of the air 80 (interfaces 80A, 80B) at a certain time but also a change in the travel speed of the air 80 (interfaces 80A, 80B) along with advancement of the time.

Note that the installation interval of the plural photo sensors 52A to 52E is selected based on the amount of blood to be caused to travel the blood filter 2, the internal diameter of the straight tube 56, etc., and is selected from distances corresponding to an amount equal to 10 to 100 μL with reference to a fluid volume. For example, when 100 μL of the blood is caused to travel the blood filter 2, the installation interval of the plural photo sensors 52A to 52E is set to be an amount corresponding to 25 μL.

Figure 2:
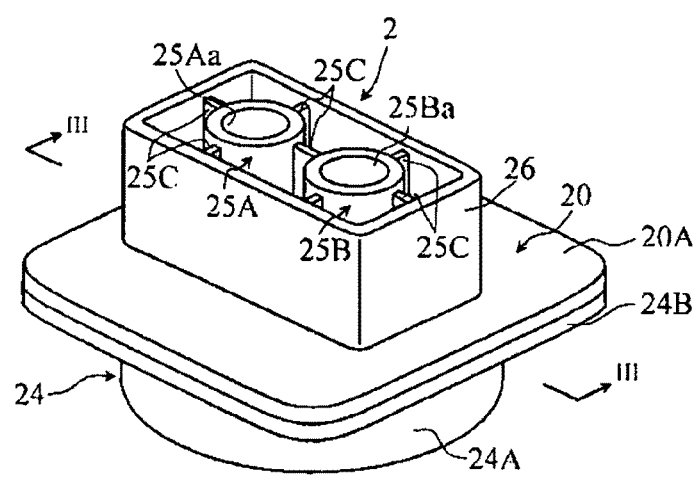
FIG. 2 is an overall perspective view for explaining a blood filter used in the blood inspecting apparatus shown in FIG. 1.

The travel speed of the air 80 depends on the travel resistance when the blood travels the fluid-channel substrate 21 in the blood filter 2 (see FIGS. 1 to 3). Accordingly, by detecting the travel speed of the air 80 (interfaces 82A, 82B) by the flow rate sensor 52, it is possible to obtain information like the flowability of the blood.

The pressure-reduction bottle 53 shown in FIG. 1 is for temporarily reserving a waste liquid, and is for defining a pressure-reduction space. The pressure-reduction bottle 53 is connected to the flow rate sensor 52 by the piping 77, and is connected to the pressure-reduction pump 54 by a piping 78. The piping 77 has a length set to have a larger internal volume than the volume of air inlet into the straight tube 56. Accordingly, in detection of traveling of the interfaces 82A, 82B, it is possible to prevent a blowout of the air 80 into the pressure-reduction bottle 53 while the interfaces 82A, 82B are caused to travel in the straight tube 56. As a result, in detection of the interfaces 82A, 82B, it is possible to suppress a change in the travel resistance against the fluid, thereby enabling appropriate detection of the travel states of the interfaces 82A, 82B.

Figure 14:
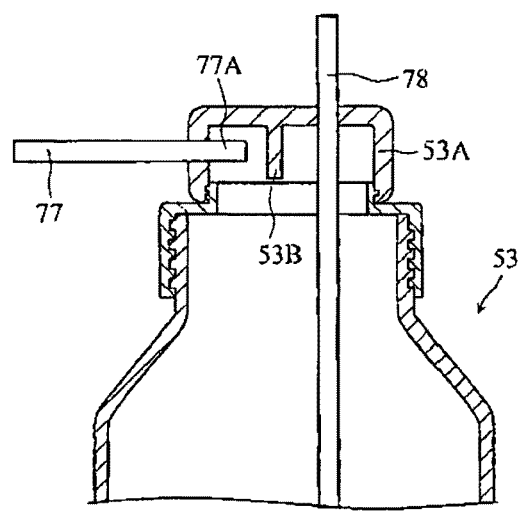
FIG. 14 is a cross-sectional view showing a major part of a pressure-reduction bottle in the blood inspecting apparatus shown in FIG. 1.

As shown in FIG. 14, the pressure-reduction bottle 53 has a cap 53A, and is connected to the pipings 77, 78 through the cap 53A. A connected part 77A of the piping 77 with the pressure-reduction bottle 53 is arranged so as to run horizontally or substantially horizontally. A connected part 78A further protrudes into the interior of the pressure-reduction bottle 54. The cap 53A has a wall 53B provided so as to face an end face of the connected part 77A of the piping 77.

In the pressure-reduction bottle 53, because the connected part 77A of the piping 77 is arranged horizontally or substantially horizontally, in comparison with a case in which the connected part is arranged vertically, a water head difference acting on the straight tube 56 can be easily and surely set to be a target value.

Arrangement of the connected part 77A protruding in the interior of the pressure-reduction bottle 53 suppresses traveling of the liquid delivered from the connected part 77A along the internal surface of the pressure-reduction bottle 53. That is, when the liquid travels along the internal surface of the pressure-reduction bottle 53, a water head difference acting on the straight tube 67 may be shifted from the set value, but protrusion of the connected part 77A can prevent the liquid from traveling along the internal surface of the pressure-reduction bottle 53.

By providing the wall 53B so as to face the end face of the connected part 77A, it is possible to prevent the liquid delivered from the connected part 77A from being splashed around the cap 53A, and the delivered liquid can be appropriately guided to the bottom of the pressure-reduction bottle 53. In addition, when the connected part 77A is arranged horizontally or substantially horizontally, by providing the wall 53B, a negative pressure can appropriately act on the connected part 77A.

The pressure-reduction pump 54 shown in FIG. 1 is for reducing the pressure inside the pressure-reduction bottle 53 in order to suction a liquid inside the blood filter 2 or to inlet the atmosphere into the piping 7A. The pressure-reduction pump 54 is connected to the pressure-reduction bottle 53 by the piping 78, is connected to the liquid discharging bottle 55 via a piping 79, and also has a function of feeding a waste liquid in the pressure-reduction bottle 53 to the liquid discharging bottle 55. Various kinds of pumps can be used as the pressure-reduction pump 56, but from the standpoint of miniaturization of the apparatus, it is preferable to use a tube pump.

The liquid discharging bottle 55 is for reserving a waste liquid in the pressure-reduction bottle 53, and is connected to the pressure-reduction bottle 53 by the pipings 78, 79.

The imaging device 6 is for picking up an image of a travel state of a blood in the fluid-channel substrate 21. The imaging device 6 comprises, for example, a CCD camera, and is arranged so as to position ahead of the fluid-channel substrate 21. An image pickup result by the imaging device 6 is output to, for example, a monitor 60, so that it is possible to check the travel state of the blood in real time or as a recorded image.

Figure 15:
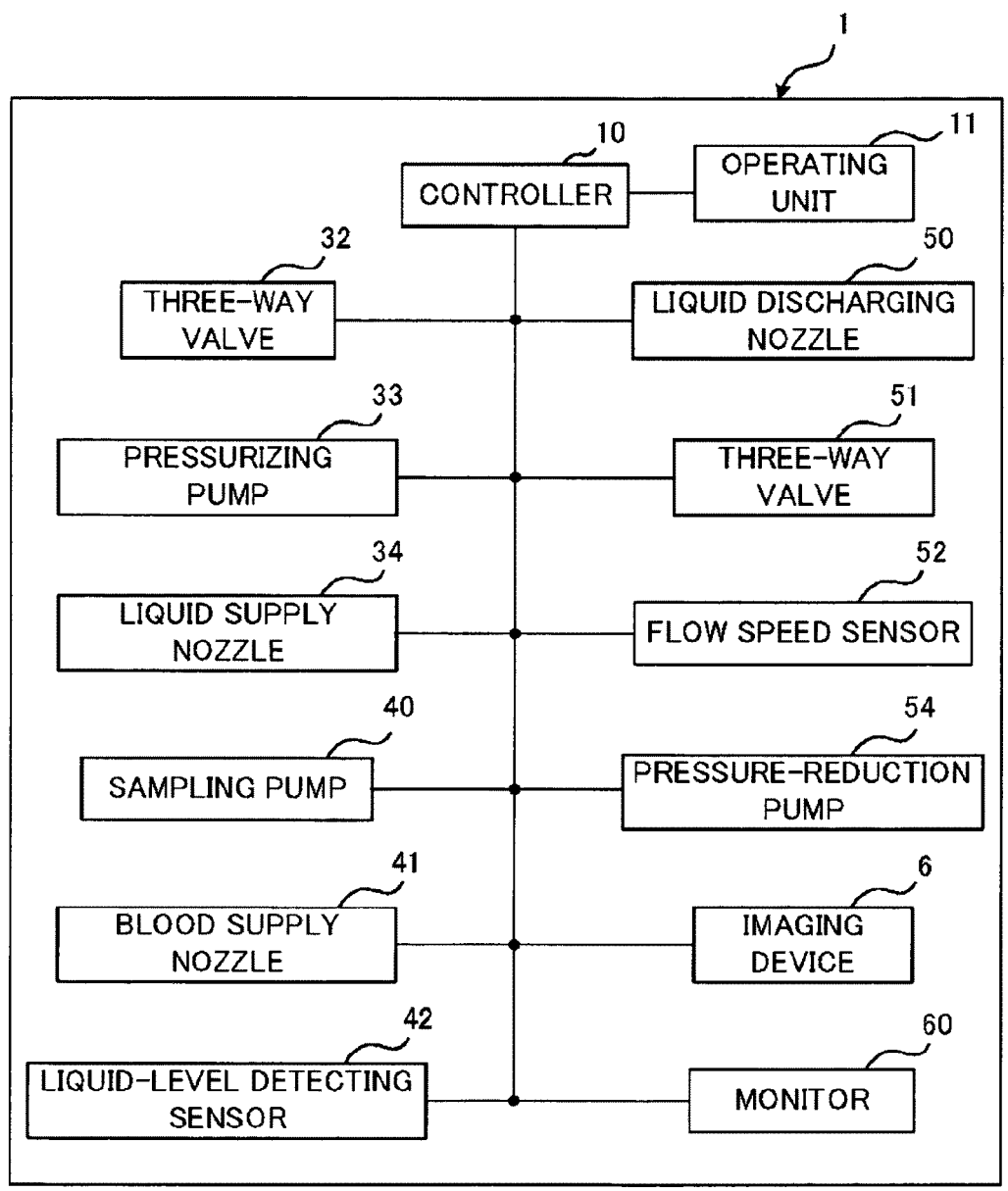
FIG. 15 is a block diagram of the blood inspecting apparatus shown in FIG. 1.

The blood inspecting apparatus 1 further includes a controller 10 and an operating unit 11 as shown in FIG. 15 in addition to the individual units shown in FIG. 1.

The controller 10 is for controlling individual units. The controller 10 performs, for example, switching control on the three-way valves 32, 51, driving control on each pump 33, 54, driving control on each nozzle 34, 41, and 50, and operation control on the imaging device 6 and the monitor 60.

The operating unit 11 performs arithmetic operation necessary for causing individual units to operate, and based on a monitoring result by the flow rate sensor 52, calculates a travel speed (flowability) of the blood in the blood filter 2.

Next, an explanation will be given of an operation of the blood inspecting apparatus 1.

Figure 16:
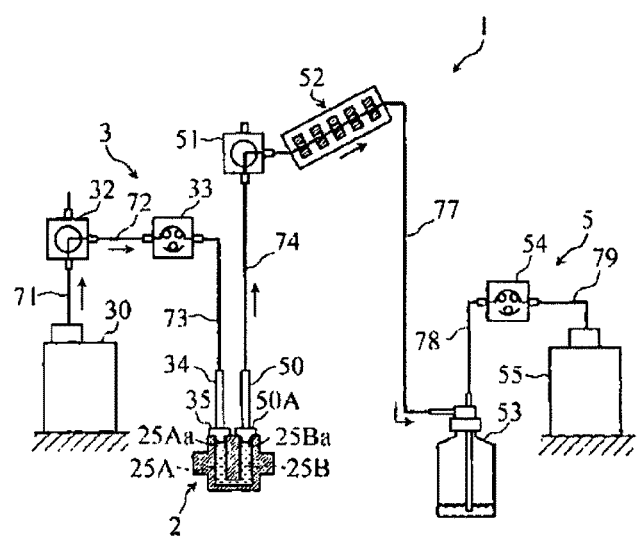
FIG. 16 is a piping diagram for explaining a gas/liquid replacement operation by the blood inspecting apparatus shown in FIG. 1.

First, as shown in FIG. 16, with the blood filter 2 being set at a predetermined position, an initiation of starting measurement is given. This initiation is given as a user operates a button of the blood inspecting apparatus 1 or is automatically given when the user sets the blood filter 2 thereto. When recognizing that the initiation of starting measurement is given, the controller 10 (see FIG. 14) performs a gas/liquid replacement operation in the interior of the blood filter 2. More specifically, first, the controller 10 (see FIG. 15) attaches the liquid supply nozzle 34 of the liquid supply mechanism 3 to the upper opening 25Aa of the small-diameter cylinder 25A in the blood filter 2, and attaches the liquid discharging nozzle 50 of the liquid discharging mechanism 5 to the upper opening 25Ba of the small-diameter cylinder 25B in the blood filter 2. Meanwhile, the controller 10 (see FIG. 15) switches the three-way valve 32 to make the bottle 30 communicated with the liquid supply nozzle 34, and switches the three-way valve 51 to make the liquid discharging nozzle 50 communicated with the pressure-reduction bottle 53. That is, the path between the bottle 30 and the pressure-reduction bottle 53 is communicated through the interior of the blood filter 2. In this state, the controller 10 (see FIG. 14) actuates the pressurizing pump 33 of the liquid supply mechanism 3 and the pressure-reduction pump 54 of the liquid discharging mechanism 5. The pressure by the pressurizing pump 33 is set to be, for example, 1 to 150 kPa, and the reduced pressure by the pressure-reduction pump 54 is set to be 0 to −50 kPa.

When the pressurizing pump 33 and the pressure-reduction pump 54 are actuated in this fashion, an isotonic sodium chloride solution in the bottle 30 is supplied to the liquid supply nozzle 34 through the pipings 71 to 73, passes through the interior of the blood filter 2, and is discharged in the pressure-reduction bottle 53 through the liquid discharging nozzle 50 and the pipings 74 to 77. The isotonic sodium chloride solution discharged in the pressure-reduction bottle 53 is discharged in the liquid discharging bottle 55 through the pipings 78, 79 by power of the pressure-reduction pump 54. Accordingly, a gas in the interior of the blood filter 2 is evacuated by the isotonic sodium chloride solution, and the interior of the blood filter 2 is replaced with the isotonic sodium chloride solution.

According to the blood inspecting apparatus 1, the gas/liquid replacement for the blood filter 2 is carried out by using the pressurizing pump 33 arranged at the upstream side of the blood filter 2 and the pressure-reduction pump 54 arranged at the downstream side of the blood filter 2. Accordingly, in comparison with a case in which only the pressure-reduction pump 54 arranged at the downstream side of the blood filter 2 is used, a possibility that air bubbles remain in the interior of the blood filter 2 is remarkably reduced, and a time necessary for evacuating the gas in the interior of the blood filter 2 can be also reduced. This enables reduction of a time necessary for a blood inspection. Moreover, according to the blood inspecting apparatus 1, although the pressurizing pump 33 is also used together with the pressure-reduction pump 54, pump power necessary for a gas/liquid replacement is reduced and a replacement time can be shortened, thereby reducing the running cost.

Figure 17:
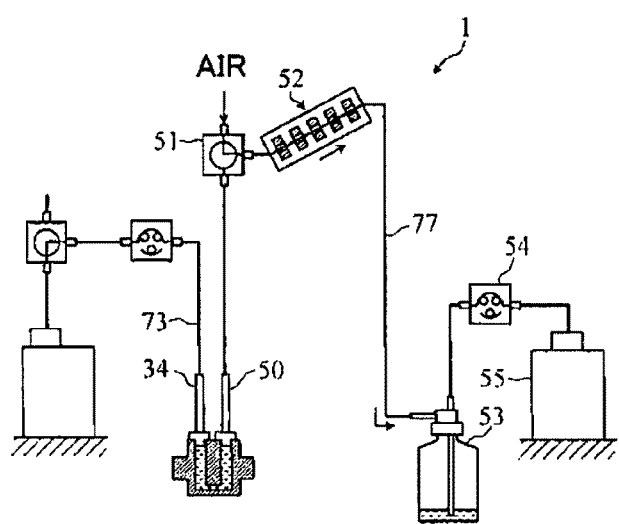
FIG. 17 is a piping diagram for explaining an air inletting operation by the blood inspecting apparatus shown in FIG. 1.
Figure 18A:
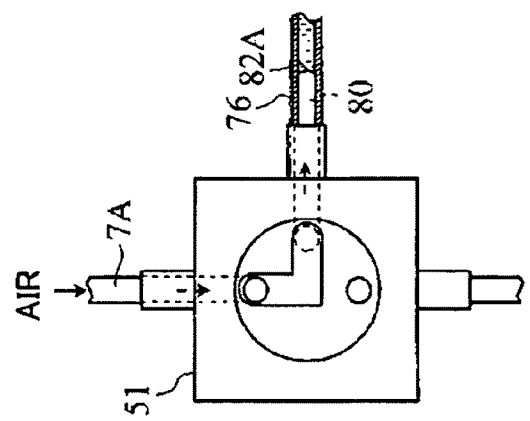
FIGS. 18A to 18C are partial transparent views for explaining the states around a three-way valve in the air inletting operation by the blood inspecting apparatus shown in FIG. 1.
Figure 18B:
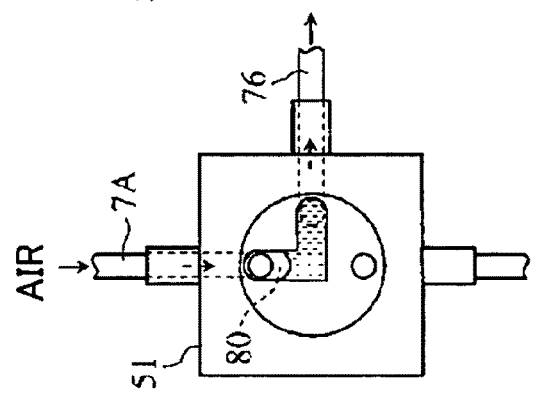
Figure 18C:
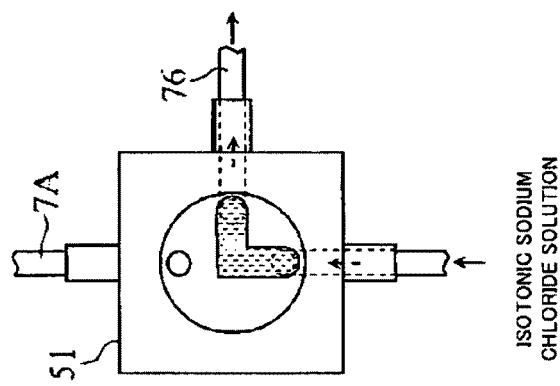

Next, in the blood inspecting apparatus 1, as shown in FIG. 17, a process of inletting air into the interior of the piping 76 is executed. More specifically, the controller 10 (see FIG. 15) stops actuating the pressure-reduction pump 54, switches the three-way valve 51 into a state shown in FIG. 18B from a state shown in FIG. 18A to make the piping 76 communicated with the atmosphere through the piping 7A. At this time, the pressure-reduction bottle 53 (see FIG. 16) is in a pressure-reduction state by the former gas/liquid replacement. Accordingly, by making the piping 76 communicated with the atmosphere through the piping 7A, because of the negative pressure by the pressure-reduction bottle 53 (see FIG. 17), as shown in FIGS. 18B and 18C, the air 80 is inlet into the piping 76 through the piping 7A. Inletting of the air 80 into the piping 76 is being carried out until the target amount of air 80 is inlet into the piping 76. The amount of air 80 to be inlet into the piping 76 is, for example, roughly same (e.g., 100 μL) as the blood to be supplied to the blood filter 2. Inletting of the air into the piping 76 is terminated by switching the three-way valve 51 when, for example, the photo sensor 52A to 52E selected beforehand detects a downstream-side interface between the air 80 and the liquid (isotonic sodium chloride solution) 81. At this time, the air 80 is present as residual air in the halfway of the liquid (isotonic sodium chloride solution) 81. That is, the liquid (isotonic sodium chloride solution) 81 is present at both upstream side and downstream side of the air 80.

Needless to say, how to terminate inletting of the air into the piping 76 is not limited to the scheme of detecting the downstream-side interface by the photo sensor 52A, and for example, it may be controlled based on an open time of the three-way valve 51 to the atmosphere.

Figure 19:
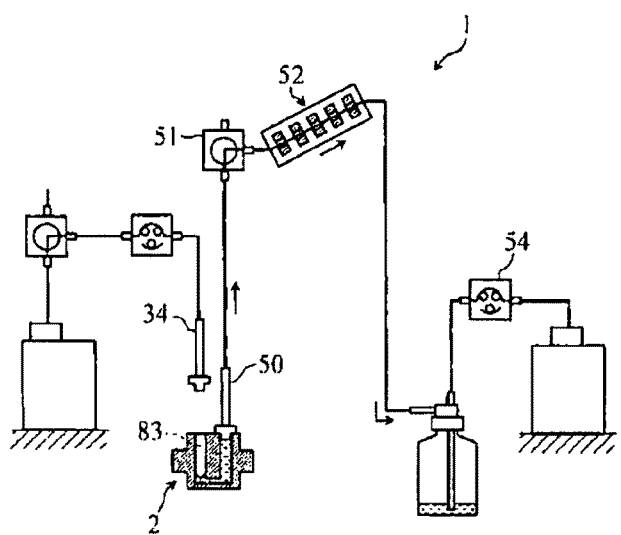
FIG. 19 is a piping diagram for explaining a liquid discharging operation for forming a space in the blood filter in the blood inspecting apparatus shown in FIG. 1.
Figure 20A:
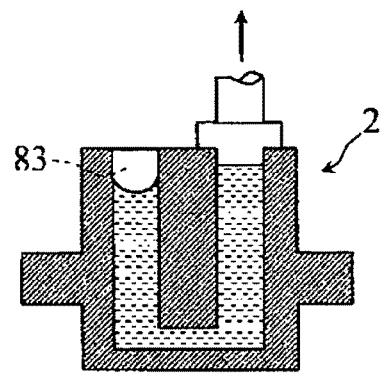
FIGS. 20A and 20B are cross-sectional views around the blood filter for explaining the liquid discharging operation.
Figure 20B:
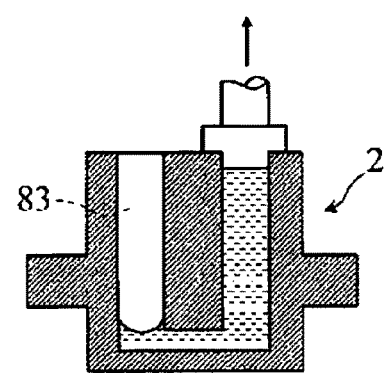

Next, as shown in FIG. 19, in the blood inspecting apparatus 1, a predetermined amount of isotonic sodium chloride solution 81 is discharged from the blood filter 2 to ensure a space 83 for retaining a blood to the blood filter 2. More specifically, the controller 10 (see FIG. 15) detaches the liquid supply nozzle 34 from the blood filter 2, and actuates the pressure-reduction pump 54. Accordingly, as shown in FIGS. 20A and 20B, the isotonic sodium chloride solution in the interior of the blood filter 2 is suctioned and eliminated through the liquid discharging nozzle 50, and an air 84 is inlet into the blood filter 2. At this time, as shown in FIGS. 21A and 21B, the isotonic sodium chloride solution 81 in the pipings 76, 77 travels toward the pressure-reduction bottle 53 (see FIG. 19), and together with this travelling, the air 80 in the piping 76 also travels toward the pressure-reduction bottle 53 (see FIG. 19).

Meanwhile, the photo sensors 52A to 52E of the flow rate sensor 52 detect a travel distance of the air 80 (interface 80A at the downstream side). In the photo sensors 52A to 52E, when the air 80 passes through, the amount of received light by the photo sensitive devices 52Ab to 52Eb is large, and when the liquid 81 passes through, the amount of received light by the photo sensitive devices 52Ab to 52Eb is small, so that by monitoring a change in the amount of received light by the photo sensitive devices 52Ab to 52Eb, the photo sensors 52A to 52E can detect the air 80 (interface at the downstream side). Thereafter, when the photo sensors 52A to 52E detect that the air 80 travels by a predetermined distance, the controller 10 (see FIG. 15) causes the isotonic sodium chloride solution and the air 80 to stop travelling.

Inletting of the air 80 through the piping 7A (see FIGS. 18A to 18C) can be terminated when, for example, the photo sensor 52A detects the interface 80A at the downstream side. Conversely, in a case in which the amount of inlet air 80 through the piping 7A is set to be roughly same as the amount of inlet blood to the blood filter 2, when the photo sensor 52A detects the interface 82A at the downstream side, the interface 82A at the upstream side can correspond to a position detectable by the photo sensor 82B.

As explained above, according to the blood inspecting apparatus 1, by detecting the position of the air 80 at the flow rate sensor 52, the amount of discharged isotonic sodium chloride solution from the blood filter 2 is regulated. Accordingly, in comparison with a case in which the amount of discharged isotonic sodium chloride solution is regulated by the liquid-level detecting sensor at the blood supply nozzle like the case of the conventional blood inspecting apparatus, it is possible for the blood inspecting apparatus 1 to regulate the amount of discharged isotonic sodium chloride solution (accomplishment of a proper interface position) within a short time. Therefore, it becomes possible to shorten a time necessary for a blood inspection.

Figure 21:
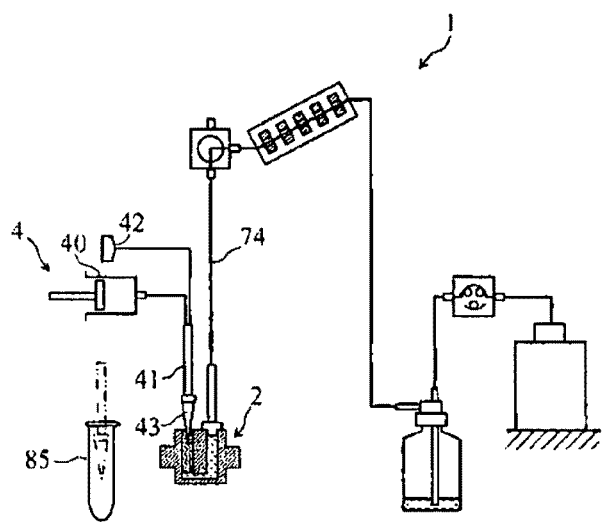
FIG. 21 is a piping diagram for explaining a blood supply operation to the blood filter in the blood inspecting apparatus shown in FIG. 1.
Figure 22A:
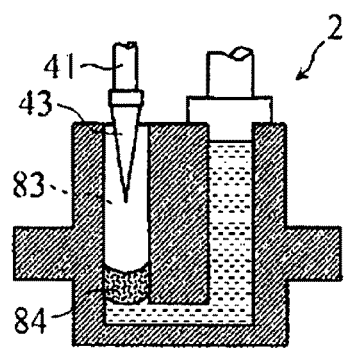
FIGS. 22A and 22B are cross-sectional views around the blood filter for explaining the blood supply operation.
Figure 22B:
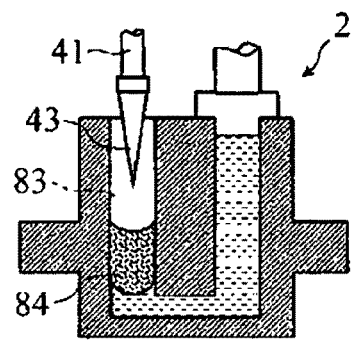

Next, as shown in FIG. 21, the controller 10 (see FIG. 15) supplies a blood 84 to the space 83 provided in the blood filter 2. More specifically, the controller 10 (see FIG. 15) suctions a blood from the blood collecting tube 85 into the interior of the chip 43 attached to the blood supply nozzle 41 by utilizing power by the sampling pump 40, and delivers the blood 84 in the chip 43 to the space 82 in the blood filter 2 as shown in FIGS. 22A and 22B. The delivery amount of blood 84 with respect to the blood filter 2 is set to be an amount corresponding to the volume of the space 83, and the delivery amount is controlled by causing the liquid-level detecting sensor 42 (see FIG. 22) to detect the liquid level of the blood in the interior of the chip 43.

Figure 23:
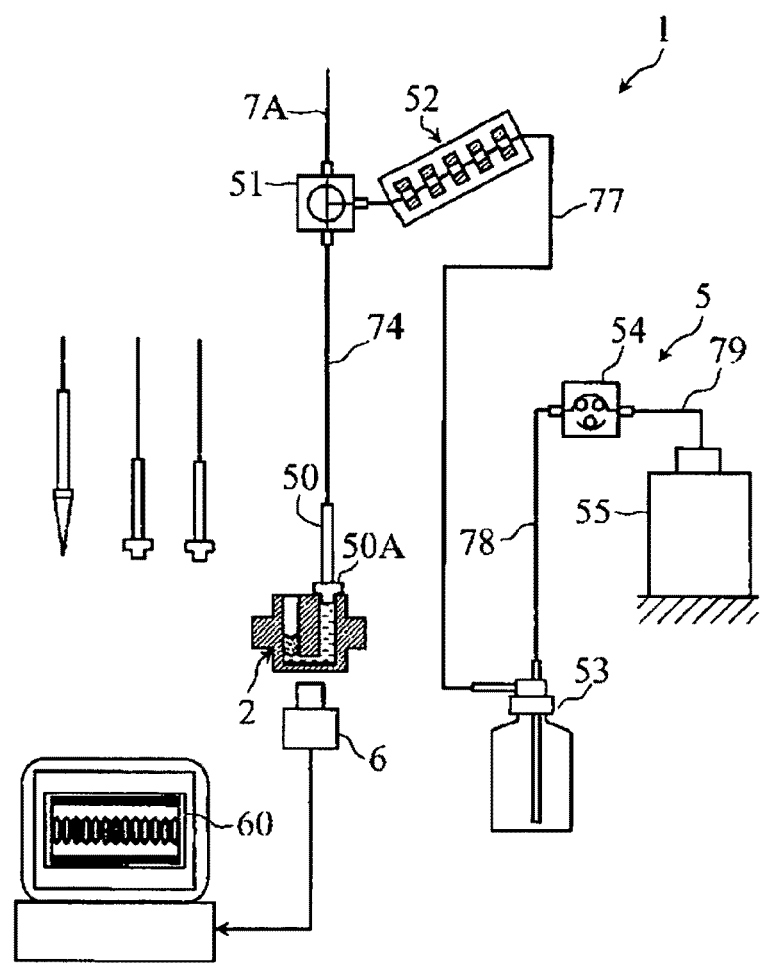
FIG. 23 is a piping diagram for explaining a measuring operation by the blood inspecting apparatus shown in FIG. 1.

Next, according to the blood inspecting apparatus 1, as shown in FIG. 23, the blood 84 supplied to the space 82 in the blood filter 2 is inspected. More specifically, the controller 10 (see FIG. 14) discharges the isotonic sodium chloride solution 81 in the blood filter 2 through the liquid discharging nozzle 50 by utilizing power by the pressure-reduction pump 54. In the meantime, in the blood filter 2, the blood 84 is moved together with the isotonic sodium chloride solution 84.

More specifically, in the blood filter 2, the blood 84 passes through a fluid channel (see FIGS. 6 to 9) formed between the fluid-channel substrate 21 and the transparent cover 23, and is moved to the small-diameter cylinder 25B. In the fluid-channel substrate 21, as is explained with reference to FIGS. 6 to 9, the blood 84 is inlet into the inlet fluid channel 28B through the through hole 28D, successively travels the communicating grooves 29 and the discharging fluid channel 28C, and is discharged through the through hole 28E. When the width dimension of the communicating groove 29 is set to be smaller than the diameter of a cell like a blood cell or a blood platelet in the blood 84, the cell travels the communicating groove 29 wile deforming, or causes the communicating groove 29 to be clogged. Such a condition of the cell is subjected to an image pickup by the imaging device 6. An image pickup result by the imaging device 6 may be displayed on the monitor 60 in real time or may be displayed on the monitor 60 after recorded.

Meanwhile, as shown in FIGS. 11 and 12, the flow rate sensor 52 monitors traveling of the interface 82B at the upstream side which travels the straight tube 56. The operating unit 11 (see FIG. 15) determines whether or not the air 80 passes through based on information obtained from each photo sensor 52A to 52E and calculates the travel speed of the air 80. The travel speed of the air 80 relates to the travel speed of the blood 84, i.e., the flowability (resistance) of the blood 84, so that the condition of the blood 84 can be figured out from the travel speed of the air 80.

Because the flow rate sensor 52 employs a structure that the straight tube 56 is inclined relative to the horizontal direction, an effect by a difference in the internal diameter of the straight tube 56 product by product affecting a measured value of a flow speed like a case in which the straight tube 56 is arranged along the horizontal direction is suppressed. Therefore, according to the inclined straight tube 56, it is possible to appropriately figure out the flow speed of the blood 83 passing through the blood filter 2. In particular, under a condition in which an effect by a difference in the internal diameter affecting the flow speed is large like a case in which the internal diameter of the straight tube 56 is set to be small so as to increase the travel speed of the air 80 in the straight tube 56, it is possible to suppress varying of the measurement precision apparatus by apparatus.

Moreover, in the blood filter 2, when the blood is caused to travel, the isotonic sodium chloride solution 81 is present at the upstream side of the air 80. On the other hand, because the piping 77 connected to the straight tube 56 has a length set to have a larger internal volume than the volume of the air 81 caused to travel the straight tube 56, the isotonic sodium chloride solution 81 is always present at the downstream side of the air 80 while the air 80 is caused to travel in the straight tube 56. Accordingly, it is possible to suppress a change in a travel resistance due to traveling of the air 80 in the piping while the blood is caused to travel. As a result, a linearity in a relationship between the travel speed of the blood 83 and the travel time thereof can be sufficiently secured, thereby making it possible to measure the travel speed of the blood 83 precisely.

In particular, if a dimension of a part where the air 80 passes through, e.g., the internal diameter of the straight tube 56 is set to be uniform (constant or substantially constant), or in addition to the straight tube 56, if respective internal diameters of the pipings 76, 77 connected to the straight tube 56 in the vicinity of the straight tube 56 are set to be same or substantially same (e.g., within a range where a different in the internal diameters with respect to the straight tube is from −3% to +3%) as that of the straight tube 56, even if the air 80 travels back and forth of the straight tube 56, it is possible to suppress a change in a contact area between the air 80 and the internal surface of the piping, thereby maintaining the contact area at constant or substantially constant.

Figure 24:
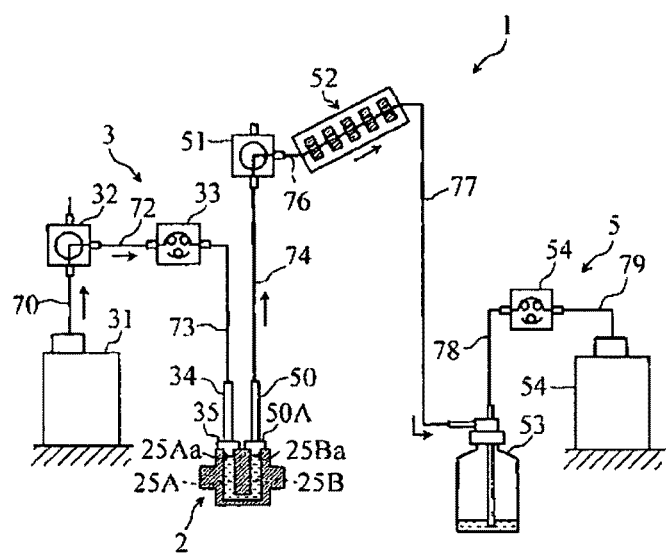
FIG. 24 is a piping diagram for explaining a rinsing operation for a piping in the blood inspecting apparatus shown in FIG. 1.
Figure 25:
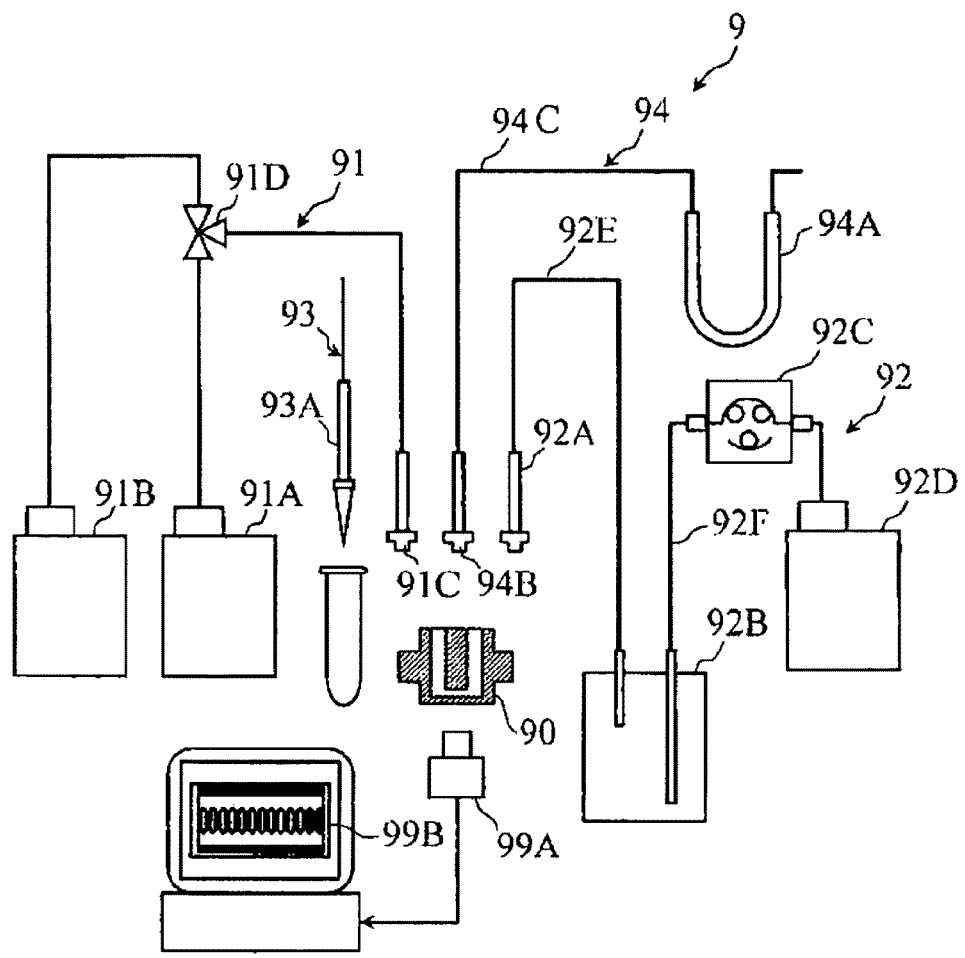
FIG. 25 is a piping diagram showing an example of conventional blood inspecting apparatus.
Figure 26:
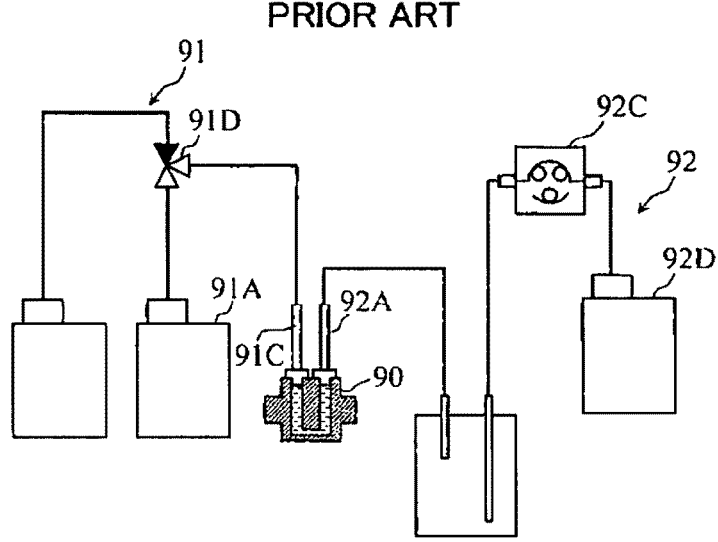
FIG. 26 is a piping diagram for explaining a gas/liquid replacement operation by the blood inspecting apparatus shown in FIG. 25.
Figure 28A:
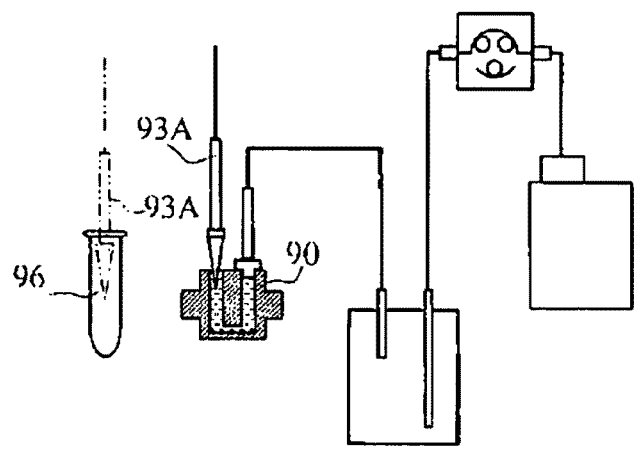
FIG. 28A is a piping diagram for explaining a blood supply operation to the blood filter in the blood inspecting apparatus shown in FIG. 25.
Figure 28B:
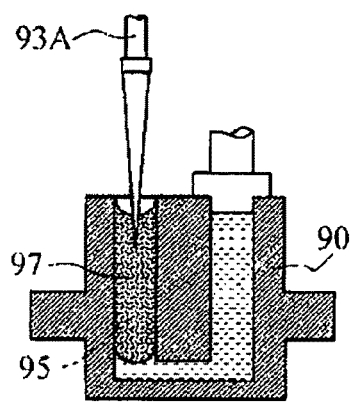
FIG. 28B is a cross-sectional view around the blood filter for explaining the blood supply operation.
Figure 29A:
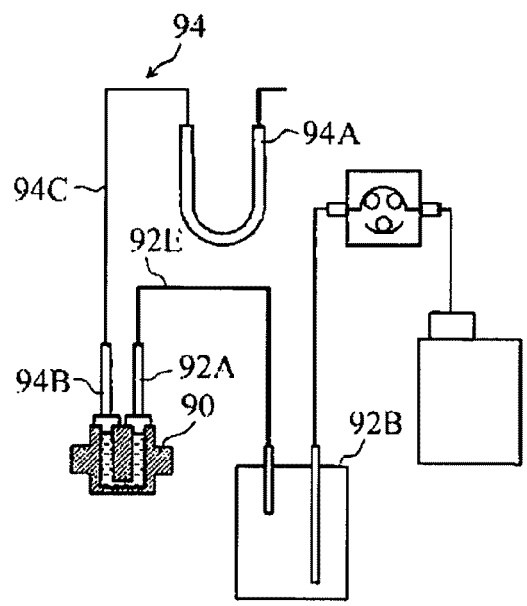
FIG. 29A is a piping diagram for explaining a measuring operation by the blood inspecting apparatus shown in FIG. 1.
Figure 29B:
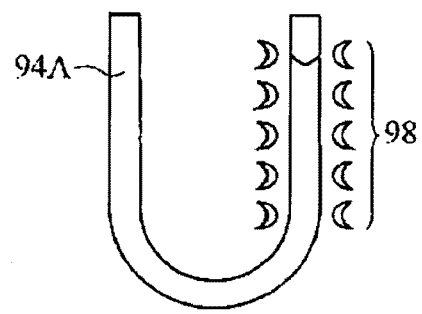
FIG. 29B is a front view for explaining a fluid-channel sensor in the measuring operation.

As shown in FIG. 24, when inspection of the blood completes, based on a selection given by the user, the pipings 73, 74, 76, and 77 of the liquid discharging mechanism 5 are rinsed. This rinsing process is carried out as the user selects a rinsing mode with a dummy chip 2' for rinsing being set at the position where the blood filter 2 is set. The dummy chip 2' has the same external shape as that of the blood filter 2, and has a communicating hole 20' provided therein. The communicating hole 20' has openings 21', 22' provided at respective portions corresponding to the upper openings 25Aa, 25Ba of the small-diameter cylinders 25A, 25B (see FIGS. 2 and 3) in the blood filter 2.

In the blood inspecting apparatus 1, when the rinsing mode is selected, the controller 10 (see FIG. 14) first attaches the liquid supply nozzle 34 of the liquid supply mechanism 3 to the opening 21' of the communicating hole 20' of the dummy chip 2', and attaches the liquid discharging nozzle 50 of the liquid discharging mechanism 5 to the opening 22' of the communicating hole 20' of the dummy chip 2'. Meanwhile, the controller 10 (see FIG. 14) switches the three-way valve 32 to make the bottle 31 communicated with the liquid supply nozzle 34, and switches the three-way valve 51 to make the liquid discharging nozzle 50 communicated with the pressure-reduction bottle 53. That is, a path between the bottle 31 and the pressure-reduction bottle 53 is communicated through the communicating hole 20' of the dummy chip 2'. In this state, the controller 10 (see FIG. 15) actuates the pressurizing pump 33 of the liquid supply mechanism 3 and the pressure-reduction pump 54 of the liquid discharging mechanism 5. The pressure by the pressurizing pump 33 is set to be, for example, 1 to 150 kPa, and the reduced pressure by the pressure-reduction pump 54 is set to be 0 to −50 kPa.

When the pressurizing pump 33 and the pressure-reduction pump 54 are actuated in this fashion, the distilled water in the liquid bottle 31 is supplied to the liquid supply nozzle 34 through the pipings 70, 72, and 73, passes through the communicating hole 20' of the dummy chip 2', and is discharged in the pressure-reduction bottle 53 through the liquid discharging nozzle 50 and the pipings 73, 74, 76, and 77. The distilled water discharged in the pressure-reduction bottle 53 is discharged in the liquid discharging bottle 55 through the pipings 78, 79 by power of the pressure-reduction pump 54. Accordingly, the pipings 73, 74, 76, and 77 in the liquid discharging mechanism 5 are rinsed by the distilled water.

According to the blood inspecting apparatus 1, the condition of the blood is figured out based on information from the flow rate sensor 52 provided at the downstream side of the blood filter 2. Accordingly, unlike the conventional blood inspecting apparatus, it is not necessary to separately provide a piping and a nozzle interconnecting the flow rate sensor 52 and the blood filter 2 from the pipings 74, and 76 through 79 of the liquid discharging mechanism 5 and the liquid discharging nozzle 50. As a result, the blood inspecting apparatus 1 can have a apparatus configuration simplified, and can be manufactured with an advantage in cost, and can be miniaturized. Moreover, because the number of nozzles and the valves subjected to drive control is reduced, the mean-time-between-failure (MTBF) can be extended. Furthermore, because the flow rate sensor 52 is provided at the halfway of the piping of the liquid discharging mechanism 5, it is not necessary to separately provide a piping for the flow rate sensor 52 from the pipings 74, and 76 through 79 of the liquid discharging mechanism 5, and the piping length necessary for a blood inspection can be shortened. Accordingly, the fluid resistance at the time of a blood inspection can be reduced, so that it becomes possible to set power necessary for actuating the pressure-reduction pump 56 at the time of a blood inspection to be small. This results in reduction of the running cost.

The invention claimed is:

1. A flow rate sensor adjustment method in an analysis apparatus including a flow rate sensor for measuring a travel time of a sample passing through a resistive body, the flow rate sensor including a tubular member with a straight part running straightly and at least one sensor for detecting an interface between a first fluid and a second fluid both traveling in the straight part, the straight part being inclined relative to a horizontal direction, the method causing the interface to travel by what corresponds to a predetermined amount of the first fluid or the second fluid and adjusting a position of the at least one sensor with respect to the traveled interface, wherein the at least one sensor includes a plurality of sensors, a sensor located at a most upstream side or a most downstream side among the plurality of sensors is aligned with respect to the interface, the interface is repeatedly caused to travel by what corresponds to a predetermined amount of the first fluid or the second fluid, and positions of the plurality of sensors other than the sensor located at the most upstream side or the most downstream side in the plurality of sensors are adjusted every time the interface is caused to travel.

2. The flow rate sensor adjustment method according to claim 1, wherein the inclined angle of the straight part is adjusted after positions of the plurality of sensors are adjusted.

3. A flow rate sensor adjustment method in an analysis apparatus including a flow rate sensor for measuring a travel time of a sample passing through a resistive body, the flow rate sensor including a tubular member with a straight part running straightly and at least one sensor for detecting an interface between a first fluid and a second fluid both traveling in the straight part, the straight part being inclined relative to a horizontal direction, wherein the flow rate sensor adjustment method includes:

measuring a travel time or a travel velocity of the first fluid or the second fluid passing through a reference tube by detecting the interface between the first fluid and the second fluid with a plurality of sensors;

measuring a travel time or a travel velocity of the first fluid or the second fluid passing through the straight part by detecting the interface between the first fluid and the second fluid with the plurality of sensors; and adjusting respective positions of the plurality of sensors except a sensor located at a most upstream side or a most downstream side among the plurality of sensors so that the travel time or the travel velocity in the straight part is set to the travel time or the travel velocity in the reference tube.

* * * * *